United States Patent [19]

Stonestrom et al.

[11] Patent Number: 4,898,471
[45] Date of Patent: Feb. 6, 1990

[54] PARTICLE DETECTION ON PATTERNED WAFERS AND THE LIKE

[75] Inventors: J. Peter Stonestrom; John L. Vaught; Armand P. Neukermans, both of Palo Alto; Herman F. Keldermann, Berkeley; Franklin R. Koenig, Palo Alto, all of Calif.

[73] Assignee: Tencor Instruments, Mountain View, Calif.

[21] Appl. No.: 248,309

[22] Filed: Sep. 19, 1988

Related U.S. Application Data

[63] Continuation of Ser. No. 64,319, Jun. 18, 1987, abandoned.

[51] Int. Cl.⁴ ............................................. G01B 11/00
[52] U.S. Cl. ................................... 356/394; 356/237; 356/338; 356/398
[58] Field of Search ............... 356/237, 336, 338, 394, 356/398

[56] References Cited

U.S. PATENT DOCUMENTS

| | | | |
|---|---|---|---|
| 3,909,602 | 9/1975 | Micko | 356/398 |
| 4,402,607 | 9/1983 | McVay et al. | 356/338 |
| 4,468,120 | 8/1984 | Tanimoto et al. | 356/237 |
| 4,579,455 | 9/1986 | Levy et al. | 356/398 |
| 4,614,427 | 9/1986 | Koizumi et al. | 356/73 |
| 4,669,875 | 6/1987 | Shiba et al. | 356/237 |

FOREIGN PATENT DOCUMENTS

253448  5/1985  Japan .

OTHER PUBLICATIONS

Peter Gise, "Principles of Laser Scanning for Defect and Contamination Detection in Microfabrication", *Solid State Technology*, Nov. 1983, pp. 163–165.

Peter Gise, "Applications of Laser Scanning for Wafer and Photoplate Inspection", *Microcontamination*, Oct.-/Nov. 1983, pp. 41–44 and 62.

Barclay J. Tullis, "A Method of Measuring and Specifying Particle Contamination by Process Equipment", *Microcontamination*, Nov. 1985, pp. 67–73 and 160–161, Dec. 1985, pp. 15–21, and Jan. 1986, pp. 51–55 and 86, (3 parts).

*Primary Examiner*—Richard A. Rosenberger
*Attorney, Agent, or Firm*—Thomas Schneck

[57] ABSTRACT

A particle detection on a periodic patterned surface is achieved in a method and apparatus using a single light beam scanning at a shallow angle over the surface. The surface contains a plurality of identical die with streets between die. The beam scans parallel to a street direction, while a light collection system collects light scattered from the surface with a constant solid angle. The position of the collection system as well as the polarization of the light beam and collected scattered light may be arranged to maximize the particle signal compared to the pattern signal. A detector produces an electrical signal corresponding to the intensity of scattered light that is colelcted. A processor constructs templates from the electrical signal corresponding to individual die and compares the templates to identify particles. A reference template is constantly updated so that comparisons are between adjacent die. In one embodiment, the templates are made up of registered positions where the signal crosses a threshold, and the comparison is between corresponding positions to eliminate periodic pattern features, leaving only positions representing particles.

21 Claims, 4 Drawing Sheets

PARTICLE DETECTION ON PATTERNED WAFERS AND THE LIKE

This is a continuation of co-pending application Ser. No. 064,319, filed on June 18, 1987.

TECHNICAL FIELD

The present invention relates to automatic methods and apparatus for detecting particles and other defects on a patterned wafer, photomask, or the like, and in particular to such optical methods and apparatus which illuminate a patterned surface and detect the character of light reflected or scattered therefrom.

BACKGROUND ART

A patterned wafer is a semiconductor wafer with a diameter of several inches and containing a few hundred integrated circuit chips or "die", each resembling an island with a rectangular grid of "streets" between islands. The present invention is a quality control measurement apparatus in which the die on a patterned wafer are inspected for particles and other defects. A particle of dirt will create a risk of failure of the integrated circuit on a die and so a die identified as having a dirt particle thereon must either be cleaned or discarded.

Previously, wafers were most often inspected for particles by operators using conventional optical microscopes. Since this process is time-consuming, labor intensive, and requires that the wafers be handled, particle inspections were performed infrequently, usually as a statistical process control measure after a process was found to be "particle-prone" to implement appropriate changes to the process. Recently, automatic foreign-particle inspection devices have been developed. For example, in a typical apparatus, a laser beam is shone vertically onto a sample and the light scattered by the foreign particles is detected by a photodetector placed at an angle above the sample. Unfortunately, if the sample has surface patterns, the patterns also scatter the light in a similar manner and it is often impossible to distinguish scattering due to particles from that due to the pattern. Accordingly, these devices are limited to inspection of foreign particles on patternless wafers.

In U.S. Pat. No. 4,441,124, Heebner uses a plurality of photodetectors in a ring system to monitor the intensity of light scattered substantially along the wafer surface. Since a patterned wafer with no particulate matter thereon will scatter substantially no light along the wafer surface, while a wafer having particulate matter thereon will scatter a portion of the light impinging thereon along the surface, the apparatus can be used to image particles contaminating the wafer surface without imaging the pattern.

In U.S. Pat. No. 4,342,515, Akiba et al. discloses a method and apparatus using polarized light for detecting particles on a surface, as for example, the surface of a semiconductor wafer. A laser beam with s-axial polarization is projected sidewards towards the wafer to be inspected. The light reflected from the wall of a bump conforming with an etched pattern area remains polarized in the s-axial direction so is intercepted by a polarizer plate. Light reflected from foreign matter is depolarized, so as to generate light waves in both the s-axial and p-axial directions, so that the p-axial polarization component passes through the polarizer plate and is detected by a transducer.

In a dual beam particle detection system, two laser beams are directed at equivalent positions on two presumably identical die. The system has two detectors, one for each beam which detects light scattered by each die. The intensities are compared, and any difference is assumed to be due to a particle. Such a system requires precise positioning to ensure that the equivalent spots on the two die are being simultaneously observed. Unfortunately, due to nonlinearities in scanning die at differing positions, the scanning control required is quite complex.

In U.S. Pat. No. 4,579,455, Levy et al. disclose a method and inspection apparatus for detecting defects in reticle or photomask having multiple patterns thereon. An illuminator illuminates a photomask to be inspected, while left and right inspection optics project images of two duplicate die patterns of the photomask onto a one-dimensional multielement detector. A stage moves the photomask at a constant velocity in a direction normal to the length of the detector to allow the detector to sequentially view the entire area to be inspected. Digitizers convert the analog signals of the detector into values which are stored temporarily in two pixel memories. To minimize the memory requirements, the pixel memories hold pixel values for only a small number of scans. As the pixel values are shifted through the pixel memories, a defect detector circuit analyzes groups of pixels representing corresponding areas of the two die patterns. Defects are detected in 3-by-3 comparison matrices of pixels by a process of area subtraction involving the calculation of error values by summing the squares of the differences of each of the 9 pixel values in the comparison matrices and in 24 adjacent matrices. If none of the 25 resulting error values is less than a threshold, a defect is assumed. Thus, this method is essentially a spatial test of pixel by pixel comparison with some allowance for misalignment built in.

It is an object of the present invention to provide a relatively fast method and apparatus which is capable of detecting particles with sizes on the order of one micron or smaller on patterned wafers, photomasks and the like.

It is another object of the present invention to provide a particle detection method and apparatus for patterned wafers, photomasks and the like, which optimizes the ratio of particle to pattern detection, which does not require the extremely accurate tracking of dual beam systems, and which reduces or eliminates problems due to nonlinearities, defocusing and scan misalignments.

DISCLOSURE OF THE INVENTION

The above objects have been met with a method and apparatus of detecting particles on a patterned wafer, photomask or other like patterned surface in which a single light beam scans over the surface and the scattering signals corresponding to adjacent die are compared. The apparatus includes a light source producing a beam directed at a wafer or like surface at a shallow angle with a scanning mechanism directing the beam onto the wafer parallel to a street direction. A light collection system is located so as to optimize the ratio of particle to pattern signal. The system collects scattered light at a constant solid angle and feeds it to a light detector for producing an electrical signal corresponding to the collected light intensity. A processor is used for constructing templates from the electrical signal corresponding to individual die of the wafer and for comparing templates to detect particles on the die. Preferably, a first polarizer causes the beam to have a polarization parallel to the wafer surface and a second polarizer filters the scattered light so that only light with a polarization parallel to the wafer surface passes to the detector.

In operation, a single light beam scans a wafer surface. Typically, the wafer has previously been aligned so that streets are substantially parallel to the direction of scanning. The beam is directed at a shallow angle with respect to the wafer surface and preferably has a polarization which is substantially parallel to the wafer surface. Light scattered from the wafer surface is collected with the above mentioned optical collection system. Preferably, the collected light has a polarization which is substantially parallel to the wafer surface, but in any case is at least substantially parallel to the beam polarization. The collected light is detected and an electrical signal corresponding to the intensity of the collected light over time is produced. The processor then constructs templates from the electrical signal and compares templates corresponding to adjacent die. Differences are considered to be due to particles on the wafer surface. Typically, the electrical signal is sampled at constant spatial intervals and those samples in which the signal is above a preselected threshold are registered along with their positions. These threshold crossings are then compared to locate particles. A reference template may be revised or updated with a new reference template being compared with a template corresponding to the next die.

The invention has the advantage over dual beam systems that it does not require extremely accurate tracking over wide fields. Further, the shallow beam angle collection system location and polarization filtering rejects most of the pattern light which is highly anisotropic, resulting in an excellent ratio of particle to pattern signal. Since the template is updated so as to compare adjacent die where possible, errors due to scan misalignments, nonlinearities and defocusing are reduced to a negligible level. The invention is relatively fast and is capable of detecting one micron size particles, and depending on the threshold, even submicron size particles.

BEST MODE FOR CARRYING OUT THE INVENTION

Figure 1:
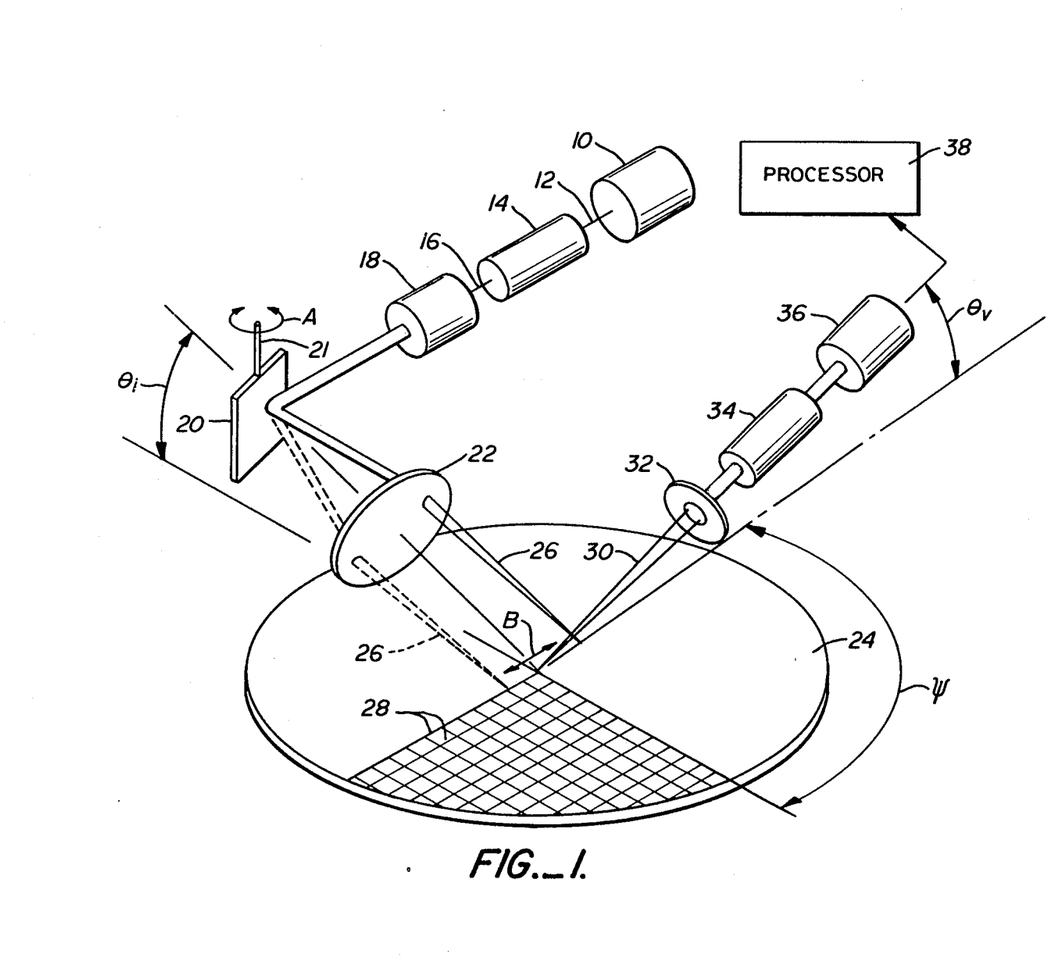
FIG. 1 is a simplified perspective view of a particle detection apparatus of the present invention.

With reference to FIG. 1, a light source 10, typically a laser, emits a beam 12. Beam 12 passes through a polarizing filter 14, such as a calcite polarizer, positioned in the beam path and becomes polarized. Alternatively, a laser light source 10 may produce a polarized beam, as in FIG. 5. The resulting polarized beam 16 has a polarization which is substantially parallel to the surface of a wafer 24. Beam 16 typically has a diameter of about 10 microns and may pass through a beam expander 18, such as a pair of lens 84 and 86 in FIG. 5, to attain a diameter as large as about 100 microns. A deflection mirror 20 pivots, as indicated by the arrows A, about an axis 21 causing the beam to scan over wafer 24 as indicated by arrows B. Final focusing optics 22, such as a Fresnel lens or concave mirror, bring the scanning beam 26 to a focus on wafer 24. The optical scanning system comprising light source 10, polarizer 14, beam expander 18, mirror 20 and focusing optics 22 is discussed further and in greater detail below with reference to FIGS. 5 and 6.

Beam 26 is directed at a shallow angle with respect to the wafer surface. This angle $\theta_i$ is typically between about 5 degrees and about 20 degrees, and preferably about 10 degrees. Because of the shallow angle of incidence, the illuminated area on the wafer is an ellipse. The ellipse has a width in the scan direction of about 20 microns and a length, in a typical range from 50 to 115 microns, preferably about 115 microns. Scanning is in a direction, indicated by arrows B which is substantially parallel to a street direction. As mentioned above, the wafer surface has a periodic pattern formed thereon representing a plurality of die with a rectangular grid of street 28 between die. One direction of the streets is aligned parallel to the scan direction. For the purposes of this invention, either of the street directions may be aligned substantially parallel to the scan direction. The wafer 24 may be aligned by hand or more usually by any of the automatic wafer alignment apparatus known in the art.

Light 30 scattered from the surface of wafer 24 is collected by a light collection system comprising collimating and focusing optics 32. Optics 32 is discussed in greater detail below with reference to FIGS. 7A and 7B. An important feature of this light collection system is that it collects an approximately constant solid angle for all points on the wafer. Typically, wafer 24 is 3 to 6 inches in diameter. Light collection which is uniform within 15% is adequate for the present invention. A polarizing filter 34, similar to polarizer 14, polarizes the collected light parallel to the surface of wafer 24. The collected light is finally detected by a detector 36, which is typically a photomultiplier tube. Detector 36 produces an electrical signal corresponding to the intensity of scattered light collected by the light collection system. This signal is directed to a processor 38, such as a microcomputer, for template construction and comparison.

The position of the light collection system is such as to receive a minimum light scattered by the pattern and thereby maximize the ratio of particle signal to pattern signal. Accordingly, the collection system is oriented to receive light 30 scattered at an elevation angle $\theta_v$ which is less than about 15 degrees above the wafer surface and at an azimuthal angle $\Psi$ relative to the incident beam direction in the range from about 80 degrees to about 100 degrees away from the direction of the incident scanning beam 26. Since the light scattered by the pattern is highly anisotropic, the azimuthal angle Ψ ensures that a minimum of pattern scattered light is collected. That which is collected may be further reduced by polarizers 14 and 34 mentioned above.

Figure 2:
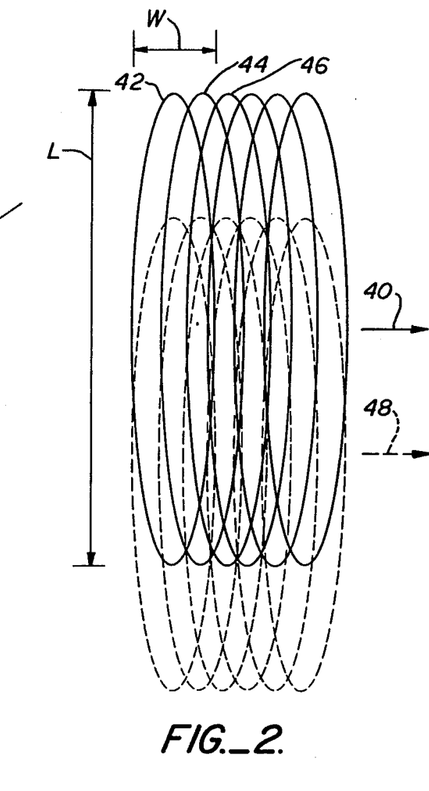
FIG. 2 is a schematic top plan illustrating the scanning of a beam over a wafer surface.

With reference to FIG. 2, the area illuminated on a wafer surface by a scanning beam is an ellipse which moves in the scan direction. The ellipse has a width W which may be 20 microns, for example. The ellipse also has a length L which may be 115 microns, for example. Two scans are seen, a first scan 40 and a second scan 48 separated by about 25 microns. During each scan, the scattered light from an illuminated area of the wafer that is detected is sampled at constant spatial intervals. The spatial position of the beam is measured by means of a sampling system described below and seen in FIG. 6. Thus, ellipse 42 represents a first sampled illumination area, ellipse 44 represents a second sampled area and ellipse 46 represents a third sampled illumination area, and so forth. The sampled elliptical areas 42, 44 and 46 overlap so as to ensure that the entire wafer is inspected. Typically, the sample interval ranges from 5 to 10 microns and would be about 5 microns for a 20 micron wide elliptical illumination area. After scanning one complete path 40, the wafer is advanced perpendicular to the scan direction and another path 48 is scanned. Scanning occurs sequentially over a plurality of adjoining paths, such as paths 40 and 48, separated by less than the width of the elliptical areas to ensure complete inspection of the wafer. Typically, the scan paths are separated by a distance of from 20 to 30 microns. For a 115 micron long ellipse, for example, paths may be separated in 25 micron increments.

Figures 3, 4:
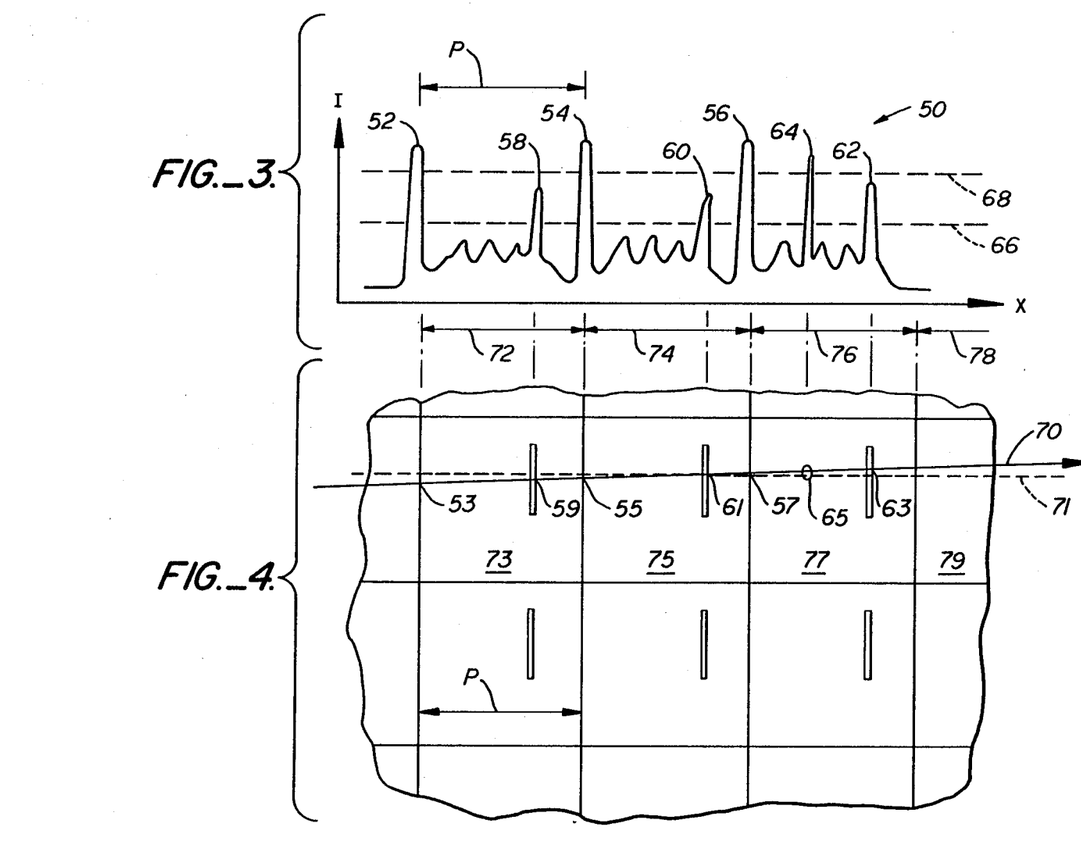
FIG. 3 is a graph of the electrical signal amplitude (I) versus beam scan position (X) on a wafer produced by the method of the present invention using the apparatus in FIG. 1.
FIG. 4 is a top plan of a portion of the wafer illustrating threshold crossings in the signal of FIG. 3.

With reference to FIGS. 3 and 4, an electrical signal 50 is produced by a detector corresponding to the intensity I of collected scattered light as a beam scans over a path 70. The abscissa X of the graph in FIG. 3 represents the spatial position of the beam on scan path 70 in FIG. 4. Signal 50 is made up of the plurality of discrete samples taken during the scan. Signal 50 has a periodicity P corresponding to the size P of the die on a wafer. Typically, the size of each die is known and accordingly, the periodicity P of the signal is also known. However, any of various known autocorrelation algorithms may be used if the periodicity is unknown or only approximately known to determine the periodicity of the signal. For a 1 cm square die, for example, 2000 samples of the collected scattered light intensity would be taken at 5 micron intervals.

Figure 5:
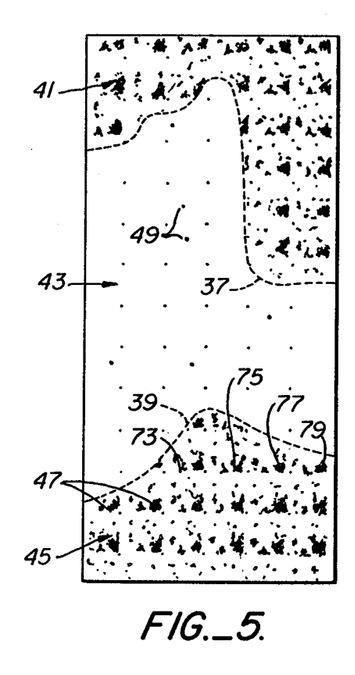
FIG. 5 is a top plan of a display derived from a scan of the wafer in FIG. 4, prior to a template comparison step of the method of the present invention.

In FIG. 5, a display resulting from a scan of the wafer in FIG. 4 has three regions of interest demarcated by dashed lines 37 and 39. A first region 41 has a high density of detected features. A second region 43 has a low density of detected features. A third region 45 again has a high density of detected features. Wafer fabrication processes may introduce variations in the patterned wafer surface which give rise to the variation in the detection density. Whether desired or not, knowledge of the variations and of the locations of different density regions may be useful information. Accordingly, raw scan information may be stored and used to form the display in FIG. 5. Also apparent in FIG. 5 are the periodic pattern features 47, including patterns corresponding to die 73, 75, 77 and 79. Detections 49 corresponding to dirt on the wafer are relatively easy to distinguish visually in the regions 41 and 45. Accordingly, the present invention processes the raw scan data using a template comparison method, discussed below.

Referring again to FIGS. 3 and 4, the peaks 52, 54 and 56 in signal 50 of FIG. 3 might correspond to wafer street crossings at points 53, 55 and 57 of paths 70 by the scanning beam. Likewise, the peaks 58, 60 and 62 in signal 50 correspond to crossings by the scanning beam over pattern features at points 59, 61 and 63 of path 70. The peak 64 corresponds to a particle at point 65 on the wafer crossed by path 70 of the scanning beam. Other signal peaks correspond to small pattern features or to particles too small to be significant. A processor receives signal 50 and constructs templates 72, 74 and 76 therefrom, each representing a die 73, 75 and 77 respectively on the wafer surface.

One form of template is the electrical signal 50 itself, made up of a plurality of samples at discrete overlapping positions on the scan and giving a representation of the collected scattered light intensity at each of the sample positions. Each template has a width equal to the die periodicity P. Thus, template 72 would be the portion of electrical signal 50 beginning at peak 52 and ending at peak 54, corresponding therefore to die 73. Another template 74 would be the portion of electrical signal 50 beginning at peak 54 and ending at peak 56, corresponding therefore to die 75. Since the two die 72 and 74, are identical except for the possible presence of particles and other defects, a comparison of the two may reveal differences which can be attributed to the particles or defects. When the templates are portions of the electrical signal 50, the differences are revealed by comparison at each sample point of the intensity value of one template from the intensity values at corresponding sample points of the other template. All differences above a preset threshold are attributed to particles or other defects. This method requires that all of the values at each sample point be retained in memory for each of two templates.

Another method of constructing a template is shown in FIG. 3, in which only those positions where the signal 50 crosses a certain threshold are stored in memory or registered, while the remaining signal portions are discarded. For example, two threshold values 66 and 68 are indicated by dashed lines in FIG. 3. At threshold 68, peaks 52, 54 and 56 are registered as well as peak 64 corresponding to particle 64. At threshold 66, peaks 58, 60 and 62 are also registered. Thus, positions that are registered, i.e. stored in memory, include both particles and periodic or quasi-periodic signals from the pattern. At the higher threshold 68 fewer positions are registered to form a template, thereby making the subsequent template comparison faster, but also risking a loss of ability to detect smaller particles. At the lower threshold 66, a greater number of positions are registered to form a template, thereby enabling smaller particles and defects to be detected but making for a slower system. Typically, the threshold 66 or 68 is preset by scanning an unpatterned wafer containing traceable polystyrene spheres of known size, typically ranging from 0.5 micron to 2.0 microns in diameter, and setting the threshold at the highest level that will consistently detect the particles of desired size.

After producing a first reference template corresponding to one die, and producing another template corresponding to a neighboring die, the templates are compared. Differences in the two templates indicate particles. For example, in the case of threshold registered templates, the registered positions in one template are compared against corresponding registered positions in the other template. In FIGS. 3 and 4, position 53 corresponding to peak 52 as part of template 72 is compared with corresponding position 55 corresponding to peak 54 as part of template 74. Since both positions are registered in their respective templates 72 and 74, they are eliminated. Similarly, registered positions 59 and 61 are eliminated. In this way, periodic signals are eliminated, leaving only the particle signals. In this instance, neither die 73 nor die 75 contains measurable particles.

After each template comparison, if no particles are detected, the reference template is revised or updated. In the present instance, reference template 72 is revised so that template 74 becomes the reference template. The steps are then repeated with the next template. Thus in FIGS. 3 and 4, templates 74 and 76 are compared, and particle 65 is detected. Since a particle is detected in die 77 corresponding to template 76, the reference template 74 is not revised to template 76 and the next comparison is between templates 74 and 78 to detect possible particles in die 79. Alternatively, the reference template may be revised after each comparison, even if a particle is detected, the existence of particles of the reference template being taken into consideration during the next comparison.

Advantages to updating the reference template are severalfold. One advantage is that extremely accurate tracking is not required and small scan misalignments are acceptable. For example, the dashed line 71 in FIG. 4 represents an ideal scan path if the wafer streets are aligned perfectly parallel to the direction of scanning by the beam. Actual scan 70 is slightly askew, so that the resulting electrical signal 50 is not perfectly periodic. When comparing templates for immediately adjacent die, such as templates 72 and 74, or templates 74 and 76, the differences in signal 50 are so slight as to be negligible. Similarly, the differences in signal 50 for templates 74 and 78 are also likely to be negligible. However, the differences between templates 72 and 78, depending on the amount of skew, may be significant enough as to produce false particle readings. Also, wafer fabrication processes may introduce a variation, such as a thickness variation in a coating, as seen in FIG. 5. Another advantage is that different lengths for the beam path for different portions of a wafer may cause defocusing problems and false readings without template updating.

Because the illuminated areas on a wafer overlap for adjacent samples in the same scan and for adjacent scans, it is possible that the same particle will be present in several of these sampled illuminated areas and so will be detected more than once. In order to ensure that there is a one-to-one correspondence between the number of particles on a wafer and the number of particles indicated by the detection apparatus, a particle position correlator is used to "fuse" separate detections of the same particle into one. One such particle position correlator and correlation method is disclosed in U.S. Pat. No. 4,641,967, assigned to the assignee of the present invention, and incorporated by reference into the present description. Briefly, the address, i.e. scan line number and Y-address, as well as the peak signal amplitude of each particle detection is stored for each scan and compared to values for matching Y-address of the next scan. The address with the largest signal amplitude is retained and are sent to computer storage.

Figure 6:
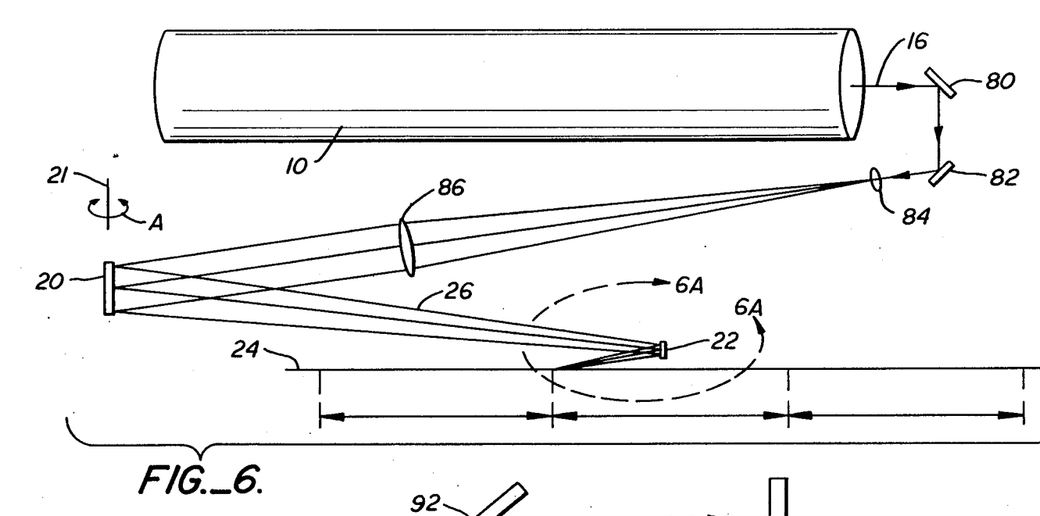
FIG. 6 is a detailed side view of the beam scanning elements of the apparatus in FIG. 1.

With reference to FIG. 6, the beam scanning system for the apparatus in FIG. 1 is seen. Laser light source 10 is typically a 3 mW multiline argon ion laser which emits at wavelengths around either 488.0 nm or 514.5 nm. Higher power 10 mW helium-neon lasers with a beam wavelength of 632.8 nm, or a helium-cadmium vapor laser with either 441.6 nm or 325 nm beams may also be used. In general, the ratio of particle to pattern signals is greater at shorter wavelengths. Beam 16, which may be emitted by the laser polarized parallel to the surface of the wafer 24 or may be polarized by a polarizer 14 seen in FIG. 1, follows a path which is folded by mirrors 80 and 82 to lenses 84 and 86. Lenses 84 and 86 together form beam expander 18 of FIG. 1. Lenses 84 and 86 may have focal lengths of 1.0 cm and 27.0 cm respectively and may be separated by 41 cm to produce a beam expansion of 40 times and a focus on wafer surface 24 at a distance of 85.0 cm. The dimensions given are exemplary and other beam expanders may be used. A scanning mirror 20 pivoting on an axis 21 in the directions indicated by arrows A is placed in the beam path about 25 cm from lens 86. A resonant flexure drive is used for the scanning mirror, providing minimum wobble. Other scanning mirrors may also be used. The path of beam 26 is lastly folded by a final focusing mirror 22 about 48 cm from scanning mirror 20 and about 9.3 cm from wafer surface 24. Focusing mirror 22 typically has a focal length of about 50 cm.

Figure 6A:
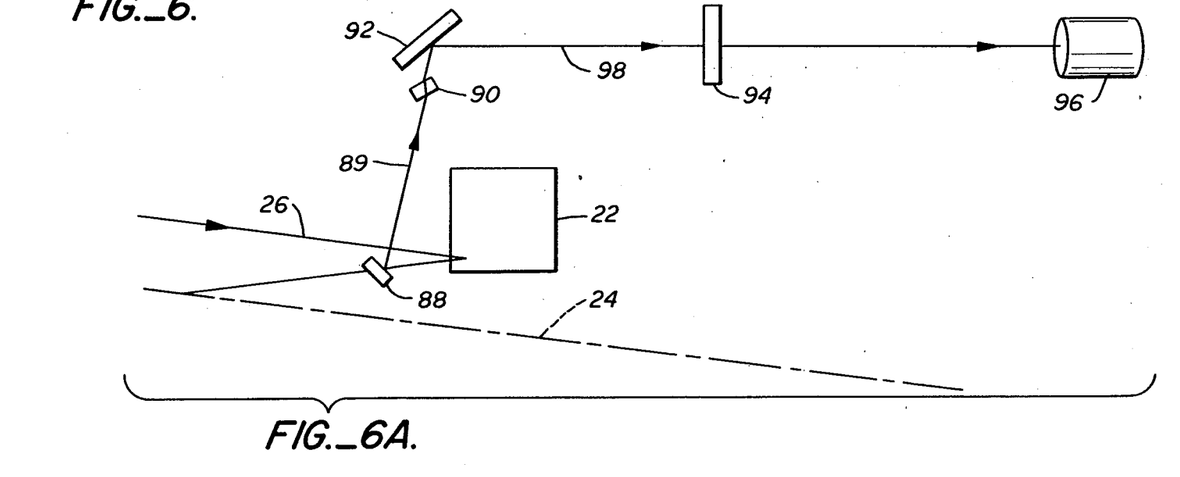
FIG. 6A is a greatly magnified view of the inside of circle 6A in FIG. 6.

With reference to FIG. 6A, a beam splitter 88 is in the path of scanning beam 26. Typically, 95 percent of the beam intensity passes through beam splitter 88 and illuminates wafer surface 24. A portion 89 of the scanning beam 26 is deflected onto a separate path and brought to a focus on a grating 90. Grating 90 is typically a Ronchi ruling with a line density of 25 line/mm. A folding mirror 92 and a Fresnel lens 94 bring various orders of beam diffraction from grating 90 onto a detector 96. Detector 96 produces an output signal which is sent to processor 38 in FIG. 1. As the beam 26 scans the wafer, beam portion 89 is incident on grating 90 at a constantly changing angle. The different orders of diffracted beam 98 are detected so as to provide a signal at 40 micron intervals for constant spatial sampling at 5 micron intervals. This is necessary because the beam velocity over the wafer varies about 20%, causing the apparent periodicity of the die spacings to vary. Grating 90 therefore ensures that signal samples are taken at constant spatial intervals.

Figure 7A:
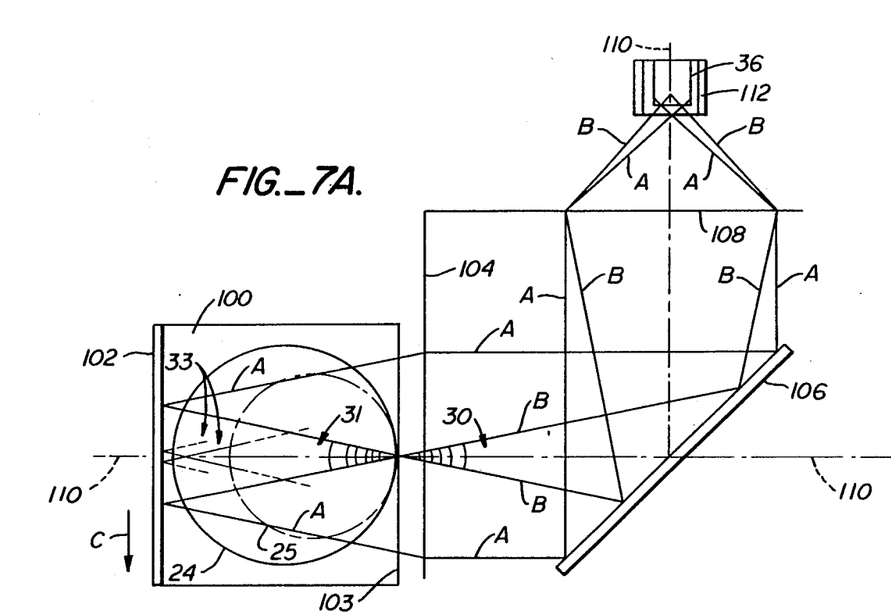
FIG. 7A is a top plan of the light collection system of the apparatus of FIG. 1.
Figure 7B:
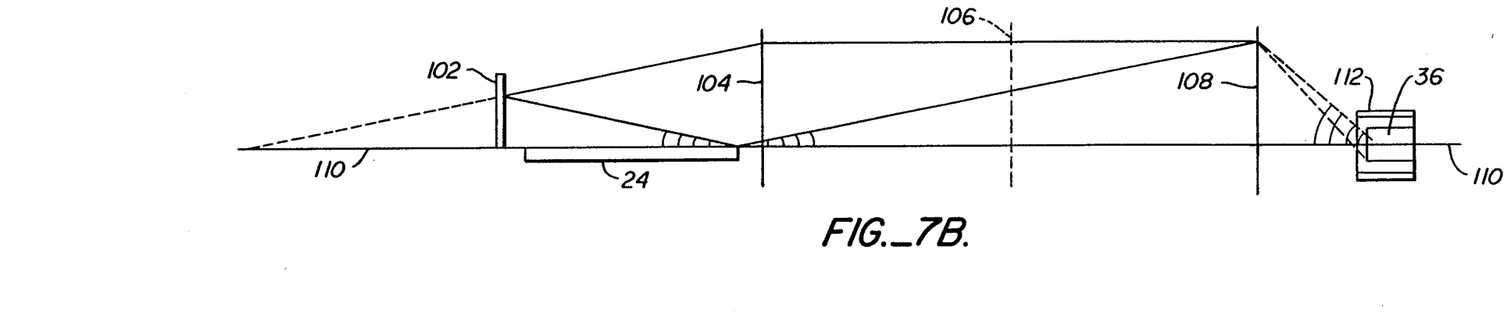
FIG. 7B is a side view of the light collection system of FIG. 7A with the light path unfolded.

With reference to FIGS. 7A and 7B, the light collection system provides a nearly constant solid angle of acceptance over the entire wafer. Light collection is uniform to within 15%. A table 100 supports a wafer 24 and moves it incrementally after each scan in the direction indicated by arrow C. Accordingly, for a first sample, light scattered within the constant solid angle cone 31 defined by lines A, and within the cone 30 defined by lines B, is collected. For the final sample, light scattered within cones 33 is collected. Table 100 supports various size wafers, such as an 8 inch wafer 24 or a 6 inch wafer 25. A mirror 102 at an edge of table 100 doubles light collection by reflecting light from cone 31, for example, back into the collection system. A lens 104 collimates the light cones. Lens 104 is located adjacent the table edge 103 opposite mirror 102, typically spaced about 9 inches from mirror 102 and about 1 inch from table edge 103. Lens 104 typically has a focal length of 18 inches.

A mirror 106 folds the optical path 110 so as to shorten the physical dimensions of the collection system. A focusing lens and field stop 108 brings the cones of light into focus on a detector 36. Typically, lens 108 is spaced about 18 inches along optical path 110 from lens 104, and has a focal length of about 3.5 inches. Detector 36 is typically a photomultiplier tube situated on optical path 110 about 3.9 inches from lens 108. Lens and stop 108 is typically a Fresnel lens. Fresnel lenses are preferred because they provide a compact system. A collection mirror can be used in place of lens 108 to collect light onto the face of the detector 36. A cylindrical shield 112 is provided around detector 36 to remove stray light and typically extends about 0.3 inch beyond the front edge of detector 36.

While the above described apparatus and method for detecting particles has been described with reference to a patterned wafer, it can easily be seen that particle detection is also possible for photomasks and other patterned surfaces, as well as unpatterned surfaces. The invention is capable of detecting particles as small as 0.5 micron on unpatterned wafers, 0.8 micron on patterned wafers without photoresist and 1.0 micron on patterned with photoresist. Generally, the smoother the surface the smaller the particles which may be detected. The invention is capable of scanning a wafer within two minutes and is somewhat tolerant of wafer misalignment.

We claim:

1. A method of particle detection on a patterned surface comprising,
    (a) scanning a substantially flat surface with a single laser beam, said beam scanning said surface in a sequence of paths,
    (b) collecting approximately constant solid angles of acceptance of light scattered from a plurality of points on said surface with an optical collection system,
    (c) detecting said collected light and producing an electrical signal corresponding to the intensity of light collected,
    (d) producing electrical waveform templates from said electrical signal, said surface having a periodic pattern representing a plurality of die formed thereon, each of said waveform templates representing a portion of a scan path corresponding to one of said die, one of said waveform templates corresponding to a die being designated as a reference waveform template,
    (e) comparing the waveform template corresponding to another die with said reference waveform template, differences between the waveform templates representing particles on the surface in said scan path, and
    (f) repeating steps (a)-(e) until at least a predetermined number of said die have been scanned.

2. The method of claim 1 further comprising updating said reference template after each comparison in step (e), said updated reference template being the template corresponding to the other die compared in step (e).

3. The method of claim 2 wherein said updating step being performed only when no particle is found in step (e).

4. The method of claim 1 wherein for producing said templates in step (d), only portions of said electrical signals above a preselected threshold value are registered.

5. The method of claim 1 wherein said beam is directed at a shallow angle with respect to said surface.

6. The method of claim 1 wherein said beam has a polarization which is substantially parallel to said surface and said collective system collects light having a polarization which is substantially parallel to said surface.

7. The method of claim 1 wherein said wafer surface pattern includes streets predominantly aligned in a street direction, said scanning by said beam being in a direction which is substantially parallel to said street direction, and said collection system is oriented to collect light scattered at a preselected azimuthal angle relative to the direction of said beam.

8. The method of claim 1 wherein said beam illuminates an elliptical area of said surface, the electrical signal corresponding to detected scattered light being sampled in spatial increments of overlapping elliptical areas, said scanning occuring sequentially over a plurality of adjoining paths separated by less than the width of said elliptical areas.

9. A method of particle detection on patterned wafers, photomasks and the like comprising,
    (a) scanning a surface with a single light beam in a sequence of paths, said beam being directed at a shallow angle with respect to said surface, said beam having a polarization which is substantially parallel to said wafer surface, said surface having a periodic pattern formed thereon representing a plurality of die with streets predominantly aligned in a street direction, said scanning being in a direction which is substantially parallel to said street direction,
    (b) collecting approximately constant solid angles of acceptance of light scattered from a plurality of points on said surface with an optical collection system, said collection system oriented in a direction to receive a minimum of light scattered by said pattern on said surface, said collection system collecting light having a polarization which is substantially parallel to said surface,
    (c) detecting said collected light and producing an electrical signal corresponding to the amount of light collected,
    (d) producing electrical waveform templates from said electrical signal, said electrical signal being approximately periodic with a period corresponding to a size of one die, each of said waveform templates representing a portion of a scan path corresponding to one die, one of said waveform templates being designated as a reference waveform template,
    (e) comparing the waveform template corresponding to another die with said reference waveform template, differences between the waveform templates representing particles of said surface in said scan path,
    (f) updating said reference waveform template with said waveform template corresponding to said other die compared in step (e), and
    (g) repeating steps (a)-(f) until all of said plurality of die are completely scanned.

10. The method of claim 9 wherein said updating step (f) occurs only if no particle is found during step (e).

11. The method of claim 9 wherein only electrical signals above a preselected threshold value are registered to produce said templates.

12. The method of claim 9 wherein said shallow angle is in the range from about 5 degrees to about 20 degrees above said surface.

13. The method of claim 9 wherein said beam illuminates an elliptical area at said surface with a width in the scan direction of about 20 microns and with a length of from 50 to 115 microns.

14. The method of claim 13 wherein said electrical signal is sampled in substantially equal increments in a range from 5 to 10 microns and wherein said laser beam scans said surface in paths separated by about 20 to 30 microns.

15. The method of claim 9 wherein said collection system is oriented in a direction which is less than about 15 degrees above the surface and receives light scattered at an azimuthal angle relative to the direction of said beam, said azimuthal angle being in a range from about 80 degrees to 100 degrees.

16. A particle detection apparatus for patterned surfaces comprising,
   a platform for holding an object with a periodic patterned surface, said surface having streets predominantly aligned in a street direction,
   a light source emitting a single light beam directed in a path toward said surface at a shallow angle,
   means in the path of said light beam for scanning said light beam in a sequence of scan paths over said surface in a direction which is substantially parallel to said street direction,
   light collection means for collecting approximately constant solid angles of acceptance of light scattered from a plurality of points on said surface, said collection means oriented in a direction to receive a minimum of light scattered by the surface pattern,
   means receiving said light from said light collection means for detecting said collected light and producing an electrical signal corresponding to the amount of light collected, and
   means in electrical communication with said detecting means for processing said signal to locate particles on said surface, said processing means including means producing electrical waveform templates from said electrical signal, each of said waveform templates representing a portion of a scan path corresponding to one of a plurality of identical die on said periodic patterned surface, one of said waveform templates being designated as a reference waveform template, said processing means also including means for comparing the waveform template corresponding to another die with said reference waveform template, differences between the waveform templates representing a particle on said surface in said scan path, said processing means further including means for updating said reference waveform template with said just compared waveform template.

17. The particle detection apparatus of claim 16 wherein said shallow angle is in the range from about 5 degrees to about 20 degrees above said surface.

18. The particle detection apparatus of claim 16 further comprising means for sampling said electrical signal at substantially equal spatial increments in a range from 5 to 10 microns, and wherein said beam scans said surface in paths separated by about 20–30 microns.

19. The particle detection apparatus of claim 16 wherein said light collection means is oriented to receive light scattered in a direction less than 15 degrees above the surface and at an azimuthal angle relative to the beam direction in a range from about 80 degrees to 100 degrees.

20. The apparatus of claim 16 wherein said light beam is directed toward said periodic patterned surface with a polarization which is substantially parallel to said surface.

21. The apparatus of claim 16 further comprising means for polarizing said collected light parallel to said surface, said beam having a polarization parallel to said surface.

* * * * *

UNITED STATES PATENT AND TRADEMARK OFFICE
CERTIFICATE OF CORRECTION

PATENT NO. : 4,898,471

DATED : February 6, 1990

INVENTOR(S) : J. Peter Stonestrom et al.

It is certified that error appears in the above-identified patent and that said Letters Patent is hereby corrected as shown below:

Title page: [75] Inventors: "J. Peter Stonestrom; John L. Vaught;" should read - - J. Peter Stonestrom, Palo Alto; Lee K. Galbraith, Mountain View; John L. Vaught; - -.

[57] Abstract, line 13, "colelcted" should read - - collected - -.

Signed and Sealed this

Twelfth Day of June, 1990

Attest:

HARRY F. MANBECK, JR.

Attesting Officer

Commissioner of Patents and Trademarks